(12) United States Patent
Suttil et al.

(10) Patent No.: US 11,335,910 B1
(45) Date of Patent: May 17, 2022

(54) ENERGY DENSE MATERIALS FOR REDOX FLOW BATTERIES

(71) Applicant: PHILLIPS 66 COMPANY, Houston, TX (US)

(72) Inventors: James A. Suttil, Honeywood (AU); Sharmila Samaroo, Benicia, CA (US); Neal D. McDaniel, Ochelata, OK (US); Jeffrey H. Drese, Owasso, OK (US); Hongjin Tan, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 5 days.

(21) Appl. No.: 17/123,300

(22) Filed: Dec. 16, 2020

(51) Int. Cl.
*H01M 4/60* (2006.01)
*H01M 8/18* (2006.01)
*H01M 8/04082* (2016.01)
*H01M 4/36* (2006.01)
*H01M 8/04186* (2016.01)
*C07D 401/04* (2006.01)

(52) U.S. Cl.
CPC ............ *H01M 4/60* (2013.01); *C07D 401/04* (2013.01); *H01M 4/368* (2013.01); *H01M 8/04186* (2013.01); *H01M 8/04201* (2013.01); *H01M 8/188* (2013.01)

(58) Field of Classification Search
CPC .... H01M 4/60; H01M 4/368; H01M 8/04186; H01M 8/04201; H01M 8/188; C07D 401/04
See application file for complete search history.

(56) References Cited

U.S. PATENT DOCUMENTS

2018/0072669 A1 3/2018 Liu et al.
2019/0173078 A1* 6/2019 Jalal .................... H01G 11/48

OTHER PUBLICATIONS

Harry D. Pratt III, Alyssa J. Rose, Chad L. Staiger, David Ingersoll and Travis M. Anderson, "Synthesis and Characterization of Ionic Liquids Containing Copper, Manganese, or Zinc Coordination Cations", Dalton Transactions, 2011, vol. 40, p. 11396-11401.
Harry D. Pratt III, Jonathan C. Leonard, Leigh Anna M. Steele, Chad L. Staiger, Travis M. Anderson, Copper Ionic Liquids: "Examining the Role of the Anion in Determining Physical and Electrochemical Properties", Inorganica Chimica Acta 396, 2013, pp. 78-83.

(Continued)

*Primary Examiner* — Stewart A Fraser
(74) *Attorney, Agent, or Firm* — Phillips 66 Company

(57) ABSTRACT

Redox flow battery efficiency and performance may be improved with a high energy density bipyridinium based ionic room-temperature liquid electrolyte. Current electrolytes require solvent to dissolve the redox-active material and a supporting electrolyte to maintain charge balance. A room temperature redox-active electrolyte having intrinsic charge balancing would not need a solvent to form a liquid and would therefore have a higher density of anions and cations involved with charge storage. As such, creating redox-active bipyridinium core ionic materials that are in a liquid form at room temperature or, more particularly, are liquids across the range at which a redox flow battery would operate permit smaller and less costly flow battery design than conventional flow batteries.

18 Claims, 14 Drawing Sheets

(56) References Cited

OTHER PUBLICATIONS

Harry D. Pratt III, David Ingersoll, Nicholas S. Hudak, Bonnie B. McKenzie, Travis M. Anderson, Copper Ionic Liquids: "Tunable Ligand and Anion Chemistries to Control Electrochemistry and Deposition Morphology", Journal of ELectroanalytical Chemistry 704, 2013, pp. 153-158.

Leo J. Small, Harry D. Pratt III, Chad L. Staiger, Travis M. Anderson, "MetILs3: A Strategy for High Density Energy Storage Using Redox-Active Ionic Liquids", Wiley-VCH, 2017, pp. 1-24.

Akihiro Shimizu, Keisuke Takenaka, Naoyuki Handa, Toshiki Nokami, Toshiyuki Itoh, and Jun-Ichi Yoshida, "Liquid Quinones for Solvent-Free Redox Flow Batteries", Advanced Materials Communication, vol. 29, pp. 1-5.

Xiaoliang Wei, Wu Xu, Murugesan Vijayakumar, Lelia Cosimbescu, Tianbiao Liu, Vincent Sprenkle, and Wei Wang, "TEMPO-Based Catholyte for High-Energy Density Nonaqueous Redox Flow Batteries", Advanced Materials, Materials Views, 2014, vol. 26, pp. 7649-7653.

Jinhua Huang, Lei Cheng, Rajeev S. Assary, Peiqi Wang, Zheng Xue, Anthony K. Burrell, Larry A. Curtiss, and Lu Zhang, "Liquid Catholyte Molecules for Nonaqueous Redox Flow Batteries", Advanced Energy Materials, Materials Views, 2015, vol. 5, pp. 1-6.

Guangtao Cong, Yucun Zhou, Zhenjun Li, and Yi-Chun Lu, "A Highly Concentrated Catholyte Enabled by a Low-Melting-Point Ferrocene Derivative", American Chemical Society, Energy Letters, 2017, vol. 2, pp. 869-875.

\* cited by examiner

ENERGY DENSE MATERIALS FOR REDOX FLOW BATTERIES

CROSS-REFERENCE TO RELATED APPLICATIONS

None.

STATEMENT REGARDING FEDERALLY SPONSORED RESEARCH OR DEVELOPMENT

None.

FIELD OF THE INVENTION

This invention relates to redox flow battery systems and more particularly to the liquids used in flow batteries.

BACKGROUND OF THE INVENTION

A redox flow battery is an electrical energy storage device that uses liquid electrolytes rather than solid electrodes to store and deliver electric power. One liquid electrolyte is called a catholyte and it is analogous to the materials that make up the cathode in a conventional, solid-state battery. The other liquid electrolyte is called the anolyte and is analogous to the materials that make up the anode of a conventional, solid-state battery. An ion transfer membrane typically separates the anolyte from the catholyte, only allowing specific ions to cross from one liquid electrolyte to the other to maintain charge neutrality during charging and discharging of the anolyte and catholyte.

The liquid electrolytes are formulated to have some molecular species with multiple states of oxidation which are stable over long time periods within a foreseeable temperature range. The cycling of these species through their accessible oxidation states during battery charge and discharge is referred to as a reduction/oxidation process, or a redox process for short.

The chemistry of potential catholyte and anolyte liquids are selected as a pair that maximize the electric density and power available in a fixed volume for a redox flow battery. Contemporary redox flow battery chemistries exhibit a maximum energy density that is on par with other technologies used for stationary energy storage. More specifically, a volumetric energy density range of 20-25 Wh/L is typical, when considering the overall combined volumes of the independent catholyte and anolyte storage tanks.

The energy density of a redox flow battery directly dictates the overall footprint of the battery, and for many applications it is desired to have as small a footprint as possible. There are continual efforts to improve energy density in redox flow batteries and reduce their effective costs to make them more competitive in our electric energy consuming world. These efforts include the exploration of high-voltage, non-aqueous chemistry, as well as that of multi-electron redox transfer chemistries.

BRIEF SUMMARY OF THE DISCLOSURE

The present invention relates to a process for making a redox flow battery including the steps of converting a bipyridinium solid to a bipyridinium containing ionic material that is liquid at a temperature below 70° C. by appending at least one substituent group to the bipyridinium where the added substituent group lowers the melting temperature of the resulting bipyridinium ionic material. An anolyte and a catholyte are provided where one of the anolyte and catholyte comprises the bipyridinium ionic material and a catholyte storage tank is provided for storing the catholyte, an anolyte storage tank is provided for storing the anolyte, a power cell is arranged for catholyte and anolyte to coexist and be physically separated while also in ion communication with one another. In addition, a catholyte pump is arranged to circulate the catholyte from the catholyte storage tank to the power cell and back to the catholyte storage tank while an anolyte pump is arranged to circulate anolyte from the anolyte storage tank to the power cell and back to the anolyte storage tank.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

Figure 1:
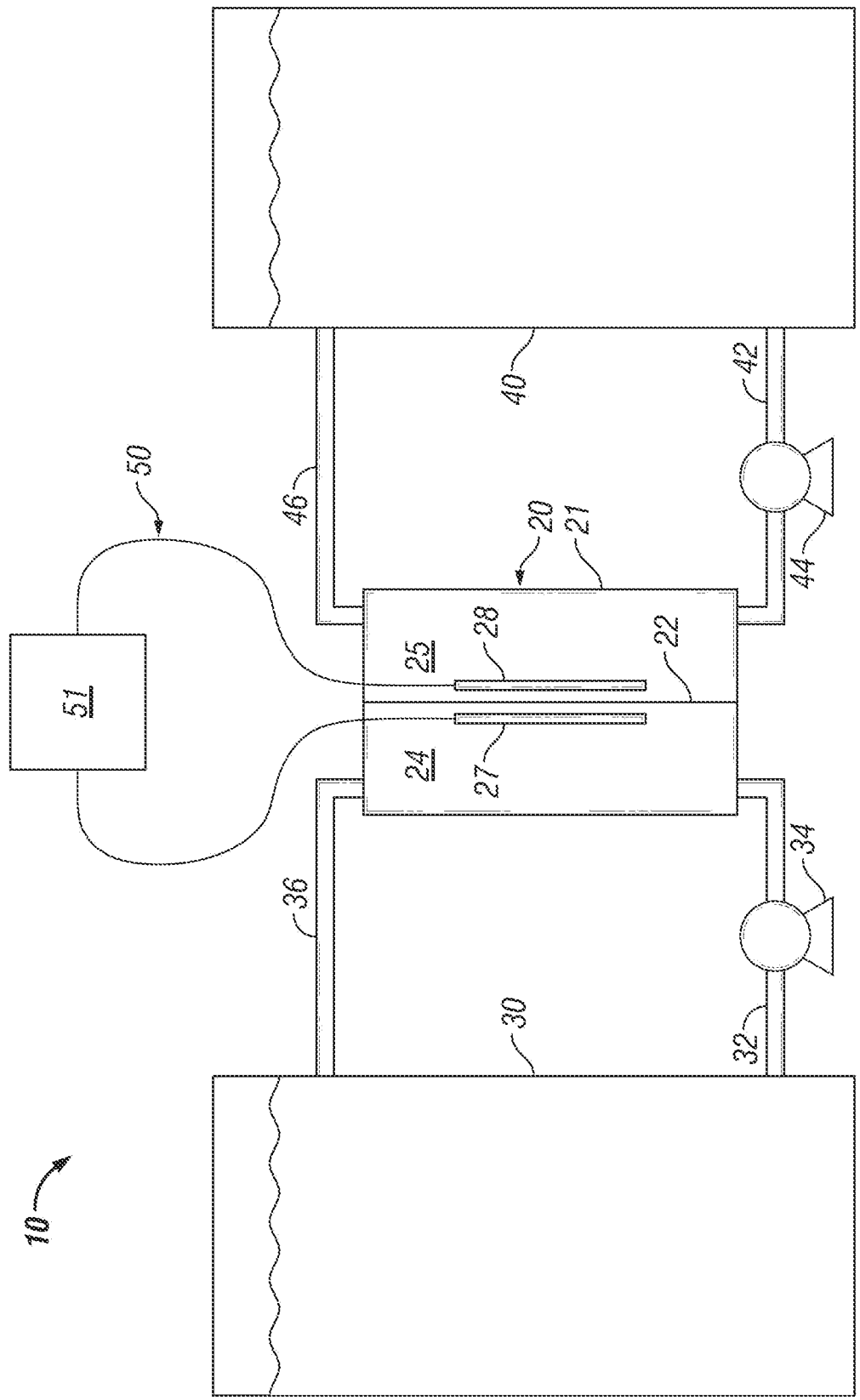
FIG. 1 is a diagram showing a basic flow battery configuration.
Figure 2:
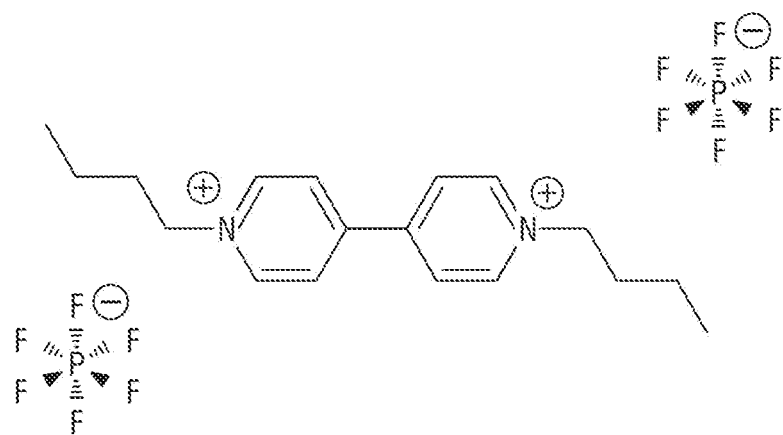
FIG. 2 is a diagram of a first chemical structural formula showing a bipyridinium form with a suitable anion that may perform as a liquid electrolyte for a redox flow battery in accordance with the present invention.
Figure 3:
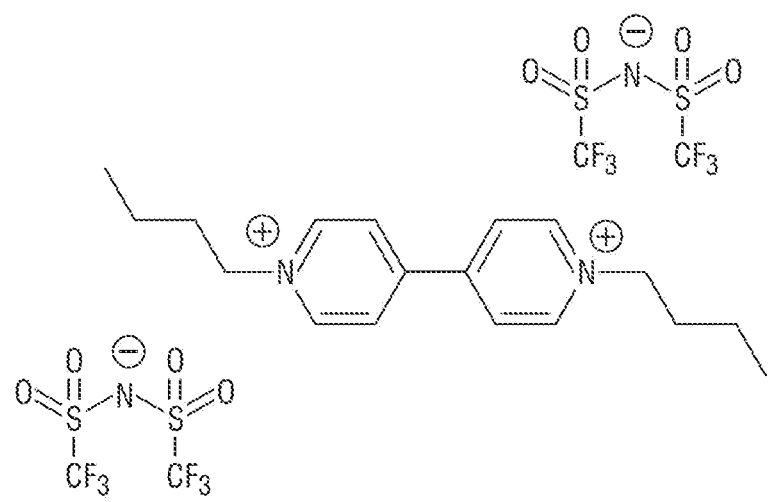
FIG. 3 is a diagram of a second chemical structural formula showing a bipyridinium form with a suitable anion that may perform as a liquid electrolyte for a redox flow battery in accordance with the present invention.
Figure 4:
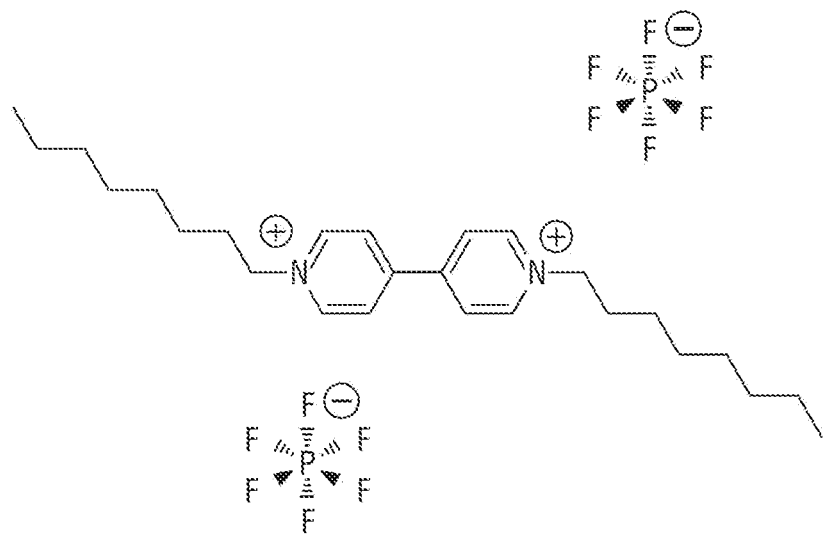
FIG. 4 is a diagram of a third chemical structural formula showing a bipyridinium form with a suitable anion that may perform as a liquid electrolyte for a redox flow battery in accordance with the present invention.
Figure 5:
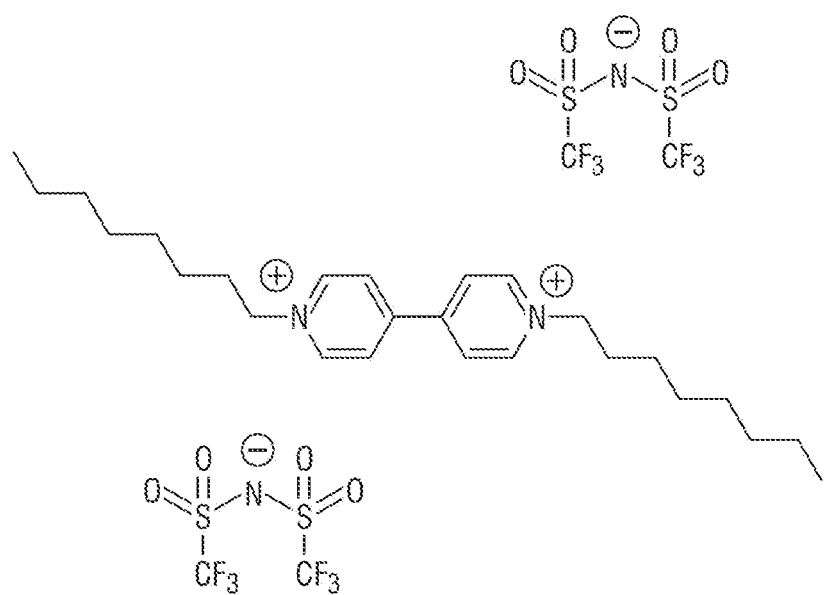
FIG. 5 is a diagram of a fourth chemical structural formula showing a bipyridinium form with a suitable anion that may perform as a liquid electrolyte for a redox flow battery in accordance with the present invention.
Figure 6:
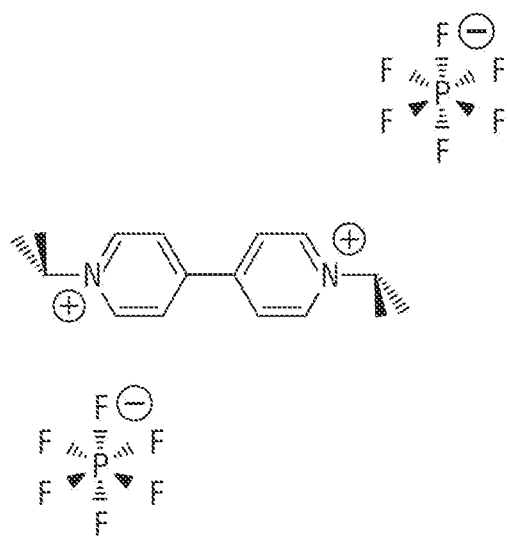
FIG. 6 is a diagram of a fifth chemical structural formula showing a bipyridinium form with a suitable anion that may perform as a liquid electrolyte for a redox flow battery in accordance with the present invention.
Figure 7:
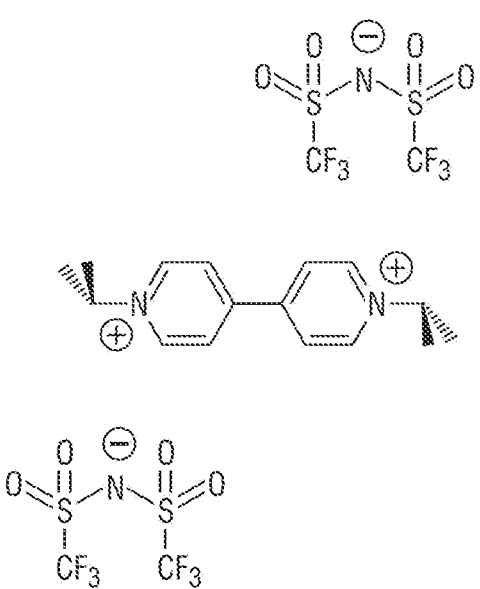
FIG. 7 is a diagram of a sixth chemical structural formula showing a bipyridinium form with a suitable anion that may perform as a liquid electrolyte for a redox flow battery in accordance with the present invention.
Figure 8:
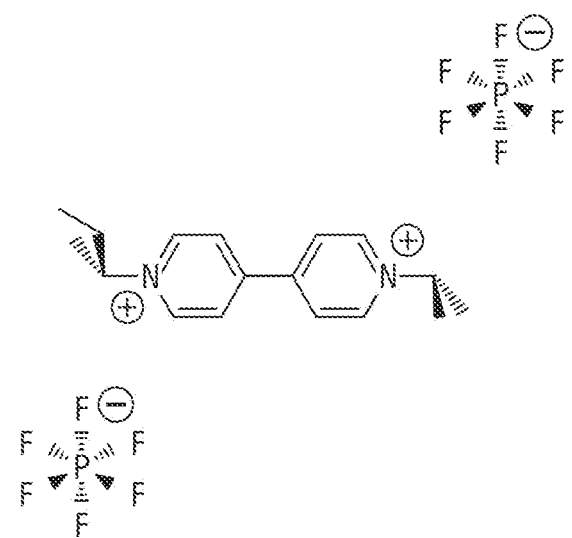
FIG. 8 is a diagram of a seventh chemical structural formula showing a bipyridinium form with a suitable anion that may perform as a liquid electrolyte for a redox flow battery in accordance with the present invention.
Figure 9:
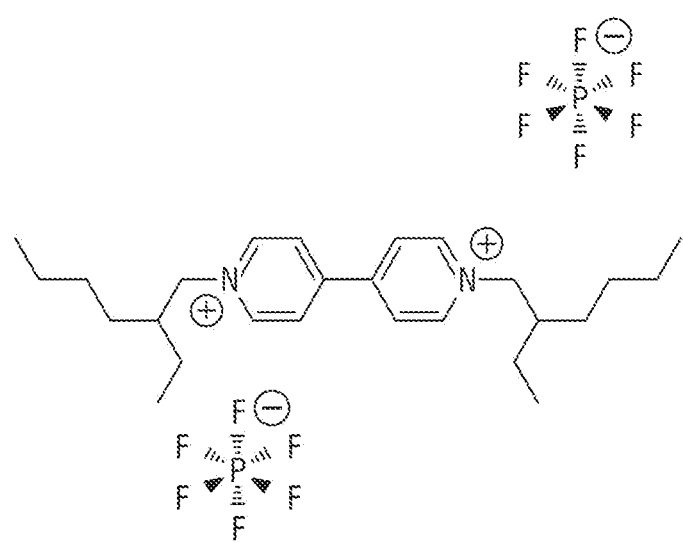
FIG. 9 is a diagram of an eighth chemical structural formula showing a bipyridinium form with a suitable anion that may perform as a liquid electrolyte for a redox flow battery in accordance with the present invention.
Figure 10:
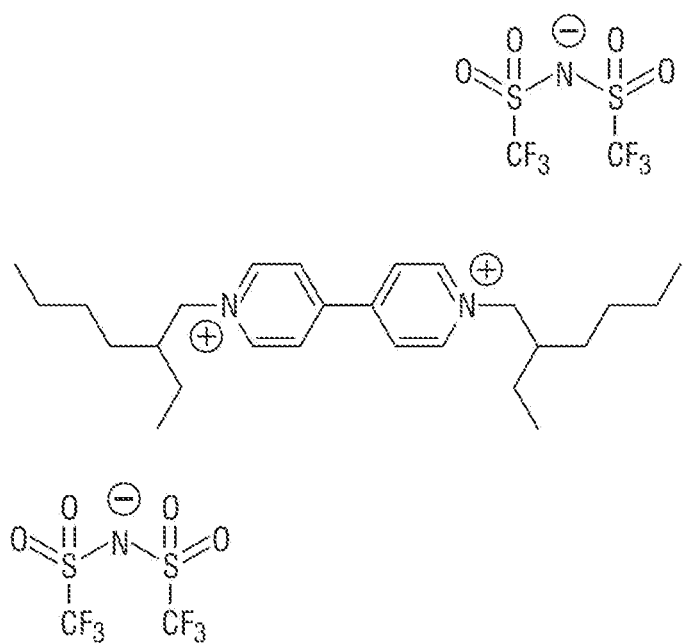
FIG. 10 is a diagram of a ninth chemical structural formula showing a bipyridinium form with a suitable anion that may perform as a liquid electrolyte for a redox flow battery in accordance with the present invention.

Turning to FIG. 1, a conventional redox flow battery is indicated by the arrow 10 with a power cell 20 at the center. The power cell 20 includes a housing 21 with an ion-selective membrane 22 dividing the housing into two compartments 24 and 25. The liquid anolyte is on the left side of the housing 21 in anolyte compartment 24 and the liquid catholyte is on the right side of the housing 21 in catholyte compartment 25. Preferably, each of the compartments 24 and 25 are substantially filled with the respective liquid electrolyte. The anolyte compartment 24 contains liquid anolyte that is continually refreshed from anolyte tank 30 via an anolyte supply conduit 32 and an anolyte circulation pump 34. Anolyte is returned from the housing 21 to the anolyte tank 30 via anolyte return line 36. Similarly, the catholyte side of the housing is supplied with liquid catholyte from catholyte tank 40 via catholyte supply conduit 42 and catholyte circulation pump 44 and the catholyte is returned to tank 40 via catholyte return line 46. Power cell 20 further includes anolyte electrode 27 and catholyte electrode 28 within their respective anolyte and catholyte and may be spaced from the ion membrane as shown or up against the membrane as long the electrodes do not present a puncture risk of the membrane. The electrodes 27 and 28 serve as electrical contacts for the flow battery 10 to be in electrical connection with a circuit 50 that includes an electric load 51.

The present invention relates to a class of materials that can be used as either anolytes or catholytes within redox flow batteries depending on the selection of the other electrolyte. It should be understood that all elements and molecular structures have varying redox potential and that it is preferred to select catholytes with substantially higher redox potential than the anolyte. The presently disclosed class are able to undergo two separate redox electron transfers. The first transfer occurs at a moderate redox potential. If a redox flow battery is designed to only access this first electron transfer, the bipyridinium electrolyte would fit in to about the center of the redox potential range making service as either a catholyte or anolyte possible. However, the second electron transfer occurs at a much lower potential, making it more applicable to be used as an anolyte. The availability of two electron transfers would make such an electrolyte a desirable choice for a redox flow battery design and hence, a bipyridinium most likely to be selected as an anolyte paired with a higher potential electrolyte being the catholyte.

The advantage of these materials is that they simultaneously fulfill the roles of solvent, redox-active material, and supporting (charge-balancing) electrolyte. In particular, the class of materials according to the present invention are known to have redox-active properties when dissolved in a solvent, but do not have high energy density owing to the presence of other materials in the liquid electrolyte. The simplicity of the present invention is that the core redox active material has been chemically modified to be a liquid at temperatures close to the operational range. At a minimum, less solvent may be used with the inventive materials netting a higher energy density making for a smaller overall redox flow battery for a common energy supply demand. In other words, with an electrolyte capable of holding and releasing more electrons per unit volume, for a standard battery need, the battery would be smaller.

The redox active ionic liquids disclosed herein can be described as having the following properties: 1) they exist in the liquid state close to an ambient temperature where the ambient temperature would depend on a localized climate, which would be at least below 70° C., but preferably be a liquid at 50° C. or less, more preferably below about 45° C. and more preferably below 35° C.; 2) they are able to undergo at least one reversible reduction/oxidation event; and, 3) they consist of a bipyridinium molecular core which in some cases may alternatively be termed mono-cationic core or di-cationic core where a di-cationic core could also be deemed a viologen chemical core. The bipyridinium core basically comprises a pair of unsaturated, 6-member carbon rings linked together at the respective first position of each ring where each carbon ring includes a nitrogen at the fourth position. The core further includes a functional group attached at least one of the nitrogen atoms or includes a second functional group attached at the other of the nitrogen atoms. In the case where there is only one functional group, it would be termed mono-substituted bipyridinium molecule as shown below:

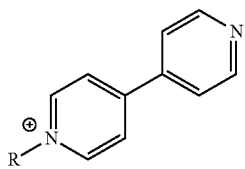

In the case where functional groups are attached at opposite ends of the core molecule, the molecule would be termed di-substituted bipyridinium molecule or, alternatively, a viologen molecule as shown below:

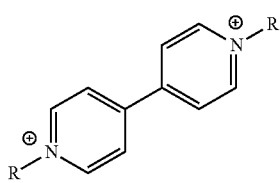

The actual chemical may take many forms with a broad array of optional appending substituents that alter the melting point of each potential redox active electrolyte chemical. Asymmetrically substituted viologens with the following characteristics: multiple redox couples, good electrochemical stability on the cyclic voltammetry timescale, and low liquefaction temperatures show promise especially with n-butyl and poly-ether functionalities combined with the viologen core and a triflimide counter-anion. The result is an energy dense redox-active room temperature ionic liquid.

As mentioned above, an important consideration for redox flow battery technologies is the energy density of the liquid electrolyte, which inversely correlates with the size of the electrolyte storage tanks and the overall footprint of the installation. Thus, there is a potential for capital cost reduction by increasing the energy density of the liquid electrolyte and minimizing the footprint. The volumetric energy density of a redox flow battery is approximately given by the following equation:

$$E = \frac{n \times V \times F \times C}{2 \times 3600}$$

where E is the volumetric energy density in W·h/L, F is Faraday's constant or 26.801 Ah/mol, V is the voltage separation between the two electrochemical half-cells in Volts, C is the limiting concentration of the electrolyte in mol/L, and n is the number of electrons transferred from one half-cell to the other per redox event. It should also be noted that the equation assumes a battery footprint dominated by the electrolyte tanks and it does not take into account the volume occupied by power cells or peripheral equipment.

For a state-of-the-art vanadium redox flow battery, the electrolyte consists of redox active vanadium salts, a supporting electrolyte (to maintain pH and charge neutrality upon battery cycling), and water as the bulk solvent. In this system, the energy density is limited to 22-24 W·h/L by the electrochemical window of water which is about 1.2 V where the number of electrons transferred makes n=1 and by the precipitation of the redox active material becomes limited in concentration at about C being 2 moles. So, by increasing the values for V, n and primarily C, one obtains a higher energy density and this approach relates to accomplishing all of the constituent roles for the electrolyte with minimal or preferably no solvent. A redox active ionic liquid according to the present invention should be a candidate to unilaterally assume the roles of bulk solvent, supporting electrolyte, and redox active species. By employing such a material, the concentration of the half-cell would be given by the density of the redox active ionic liquid and be, correspondingly, maximized. Additionally, the number of redox couples (n) may be increased through intelligent choice of the redox active core. Finally, removal of the bulk solvent eliminates the restriction due to the electrochemical degradation of the solvent and has the potential to increase the voltage of the RFB depending on the choice of the chemistry in each half-cell. So, as noted above, the invention relates to converting these redox active materials from a solid-state material at room temperature to a redox active ionic liquid through chemical modification.

Examples

For the invention, a number of compounds comprising a viologen core were synthesized and are shown in FIGS. 2-24. Initial melting point measurements were measured for each of the synthesized compounds and are shown in Table 1, below:

TABLE 1

| Compound as shown in FIG.: | Melting Point (° C.) |
|---|---|
| 2 | 176 |
| 3 | 86 |
| 4 | 67 |
| 5 | 137 |
| 6 | >250 |
| 7 | 148 |
| 8 | >250 |
| 9 | >250 |
| 10 | 94 |
| 11 | 117 |
| 12 | 99 |
| 13 | 33 |
| 14 | 42 |
| 15 | 179 |
| 16 | 50 |
| 17 | 120 |
| 18 | >250 |
| 19 | 110 |
| 20 | 225 |
| 21 | Liquid |
| 22 | 129 |
| 23 | Liquid |
| 24 | 80 |

TABLE 1-continued

| Compound as shown in FIG.: | Melting Point (° C.) |
|---|---|

Figure 21:
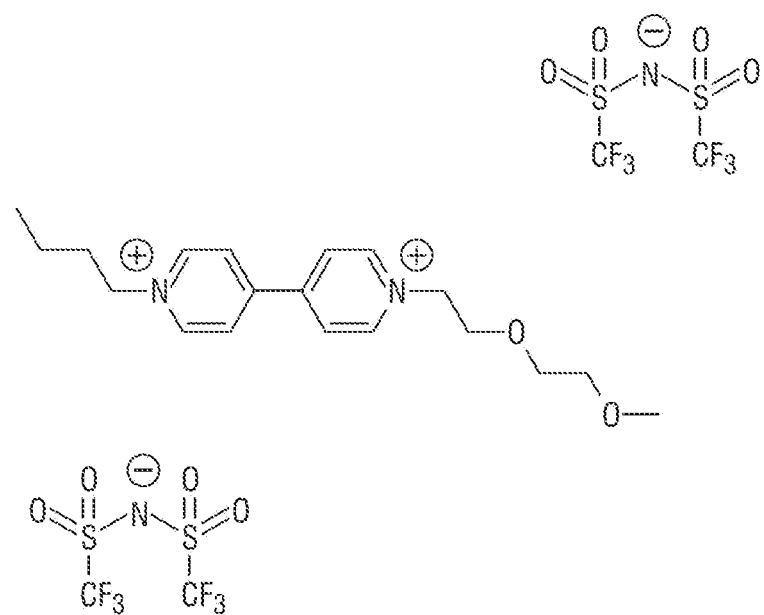
FIG. 21 is a diagram of a twentieth chemical structural formula showing a bipyridinium form with a suitable anion that may perform as a liquid electrolyte for a redox flow battery in accordance with the present invention.

Focusing on the compound shown in FIG. 21 which is a liquid at least down to a normal operating range for a redox flow battery, provides an interesting example for study having the chemical name: n-butyl-n'-(2-(2-methoxyethoxy) ethyl)-4,4'-bipyridinium triflimide. This compound combines the redox active material, supporting electrolyte and bulk solvent into a singular molecular species. As such, the concentration of (C) of the half-cell is given by the density of the redox active ionic and is maximized as there is no need to dilute the material with a bulk solvent. Secondly, n is increased by the choice of viologen redox active core which undergoes two redox events (n=2) at −0.82V and −1.27V as compared to the common Ag/Ag$^+$ reference electrode. Thirdly, removal of the bulk solvent removes the restriction around solvent degradation and has the potential to increase the voltage of the redox flow battery depending on the choice of chemistry in the second half-cell.

The preparation of the compound shown in FIG. 21 is as follows: A gram (1.00 g, 0.0064 mol) of 4,4'-bipyridine was combined with 3.64 mL (0.0320 mol) of iodobutane in 25 mL of toluene and heated to 100° C. overnight with stirring and with an air condenser in place. The mixture was cooled to room temperature and further cooled using an ice water bath for 30 minutes. The yellow solid was collected via a vacuum filter station for 15 minutes and then transferred to a 100 mL pear shaped flask where it was dissolved in 25 mL of acetonitrile with stirring. Added to the flask was 1.293 mL (0.0096 mol) of 2-(2-methoxyethoxy)ethyl bromide and then the flask was fitted with an air condenser before refluxing under nitrogen for five days. The resulting orange precipitate was collected via a vacuum filtration, washed with three 50 mL portions of diethyl ether and then air dried. The dry solid was transferred to a 100 mL pear-shaped flask and dissolved into 25 mL of deionized water with stirring. To this was added dropwise 9.2 grams of lithium bis(trifluoromethanesulfonamide) that was dissolved in to 25 mL of deionized water via a pressure equalizing dropping funnel. The resulting cream suspension was heated to 60° C. overnight to give a brown oil. The supernatant was decanted, and the brown oil was washed with excess deionized water to remove any remaining lithium iodide, lithium bromide, or lithium bis(trifluoromethanesulfonamide). This yielded 1.741 g (31%) of n-butyl-n'-(2-(2-methoxyethoxy)ethyl)-4,4'-bipyridinium triflimide.

The elemental analysis of this compound is shown in Table 2 below:

TABLE 2

| Element | Calculated Content (%) | Measured Content (%) |
|---|---|---|
| Carbon | 31.51 | 30.37 |
| Hydrogen | 3.22 | 3.42 |
| Nitrogen | 6.39 | 6.32 |
| Sulfur | 14.63 | 14.22 |

The mass to charge ratio of this compound is predicted as [M−2 NTf$_2$]$^{2+}$=158.1075 m/z and the measure by mass spectrometry was 158.1069 m/z.

The measured mass to charge ratio oft select compounds shown in the Figures are set forth in Table 3, below:

TABLE 3

| Compound as shown in FIG.: | Fragment (m/z) |
|---|---|
| 4 | [M − 2 PF$_6$]$^{2+}$ = 191.1667 |
| 13 | [M − 2 PF$_6$]$^+$ = 326.2728, [M − 2 PF$_6$]$^{2+}$ = 163.1356 |
| 14 | [M − 2 NTf$_2$]$^{2+}$ = 163.1356 |
| 16 | [M − 2 NTf$_2$]$^{2+}$ = 128.0961 |
| 21 | [M − 2 NTf$_2$]$^{2+}$ = 158.1069 |
| 23 | [M − PF$_6$]$^+$ = 213.1384 |

The electrochemical properties of select compounds shown in the Figures are set forth in Table 4, below:

TABLE 4

| Compound as shown in FIG.: | $E_1$ (V) (Redox Event 1) | $I_{pa1}$ (µA) | $I_{pc1}$ (µA) | $I_{pa1}/I_{pc1}$ | $E_2$ (V) (Redox Event 2) | $I_{pa2}$ (µA) | $I_{pc2}$ (µA) | $I_{pa2}/I_{pc2}$ |
|---|---|---|---|---|---|---|---|---|
| 4 | −1.27 | 119 | 116 | 1.03 | −0.82 | 115 | 117 | 0.99 |
| 13 | −1.27 | 172 | 162 | 1.06 | −0.83 | 169 | 162 | 1.05 |
| 14 | −1.28 | 170 | 156 | 1.09 | −0.83 | 161 | 138 | 1.17 |
| 16 | −1.28 | 210 | 197 | 1.07 | −0.83 | 206 | 195 | 1.06 |
| 21 | −1.27 | 193 | 162 | 1.19 | −0.82 | 183 | 171 | 1.07 |
| 23 | −2.11 | 404 | 253 | 1.60 | −1.36 | 409 | 334 | 1.23 |

The general preparation method for symmetrically substituted viologens shown in FIGS. 2-7 and FIGS. 9-12 is as follows: A solution of 4,4'-bipyridine (1.00 g, 6.40 mmol) and five equivalents of the desired alkyl halide were combined in a 25 mL pear-shaped flask with a stir bar. The flask was sealed with a rubber septum that was pierced with a syringe needle and then was heated to 120° C. with stirring overnight. The reaction was cooled to room temperature and 15 mL of acetonitrile was added to the mixture. The flask was then fitted with a condenser and sealed with a rubber septum pierced by a syringe needle. The reaction mixture was heated under reflux overnight at 110° C. (oil bath temperature) with stirring. A dark red precipitate formed. The mixture was cooled in an ice bath and then the solid was isolated by vacuum filtration. The solid was washed with 3×25 mL of toluene followed by 3×25 mL hexanes. The solid was then transferred to a 100-mL pear shaped round bottom flask and dissolved in 25 mL deionized water with stirring. The flask was fitted with a pressure equalizing dropping funnel loaded with five equivalents of the counter-ion exchange salt (lithium bis(trifluoromethanesulfonamide) or ammonium hexafluorophosphate) dissolved in 25 mL of deionized water. The solution was added dropwise to the functionalized bipyridinium solution. During this addition, an off-white precipitate began to form. After complete addition of the counter-ion solution, the reaction mixture was heated to 60° C. and stirred overnight. The mixture was cooled in an ice bath, the solid was then isolated by vacuum filtration, and washed with 3×25 mL of deionized water. Impure materials were further purified by dissolving the crude product in acetone and treating with excess counter-ion exchange salt until a colorless solution is achieved. The pure product could then be isolated by addition of deionized water to precipitate a colorless solid.

The general preparation method for asymmetrically substituted viologens shown in FIGS. 8, 13-19 and 21 is as follows: A solution of 4,4'-bipyridine (1.00 g, 6.40 mmol) and five equivalents of n-iodobutane (5.89 g, 32.0 mmol) were combined with 25 mL of toluene in a 100-mL round bottom flask and a stir bar. The flask was sealed with a rubber septum that was pierced with a syringe needle and the reaction mixture was heated to 100° C. with stirring, overnight. The resulting yellow suspension was then cooled in an ice bath, the solid was isolated by vacuum filtration and washed with three 3×25 mL volumes of toluene followed by 3×25 mL volumes of hexane. The yellow solid was transferred to a 100-mL pear shaped round bottom flask with 30 mL acetonitrile and five equivalents of the second alkyl halide (32.0 mmol). The flask was fitted with a condenser and the reaction mixture was heated to 110° C. overnight (oil bath temperature). The mixture was then cooled in an ice bath, the solid was isolated by vacuum filtration, and was washed with 3×25 mL volumes of toluene followed by 3×25 mL volumes of hexane. The solid was transferred to a 100-mL pear shaped round bottom flask and dissolved in 25 mL deionized water with stirring. The flask was fitted with a pressure equalizing dropping funnel loaded with five equivalents of the counter-ion exchange salt (lithium bis(trifluoromethanesulfonimide) or ammonium hexafluorophosphate) dissolved in 25 mL of deionized water. The solution was added dropwise to the functionalized bipyridinium solution. During this addition, an off-white precipitate began to form. After complete addition of the counterion solution, the reaction mixture was heated to 60° C. and stirred overnight. The mixture was cooled in an ice bath, the solid was then isolated by vacuum filtration, and washed 3×25 mL of deionized water. Impure materials were further purified by dissolving the crude product in acetone and treating it with excess counter-ion exchange salt until a colorless solution is achieved. The pure product could then be isolated by addition of deionized water to precipitate a colorless solid.

Figure 22:
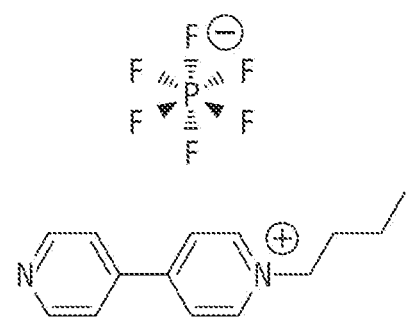
FIG. 22 is a diagram of a twenty-first chemical structural formula showing a bipyridinium form with a suitable anion that may perform as a liquid electrolyte for a redox flow battery in accordance with the present invention.
Figure 23:
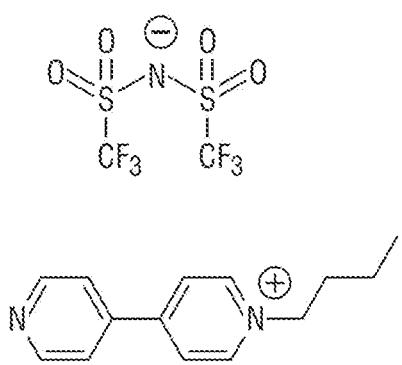
FIG. 23 is a diagram of a twenty-second chemical structural formula showing a bipyridinium form with a suitable anion that may perform as a liquid electrolyte for a redox flow battery in accordance with the present invention.

A general preparation method for the mono-substituted 4,4'-bipyridinium salts that are shown in FIGS. 22-23: A solution of 4,4'-bipyridine (1.00 g, 6.40 mmol) and five equivalents of n-iodobutane (5.89 g, 32.0 mmol) were combined with 25 mL of toluene in a 100-mL round bottom flask and a stir bar. The flask was sealed with a rubber septum that was pierced with a syringe needle. The reaction mixture was heated to 100° C. and stirred overnight. The yellow suspension was then cooled in an ice bath, the solid was then isolated by vacuum filtration, and washed with 3×25 mL volumes of toluene and 3×25 mL volumes of hexane. The solid was then transferred to a 100-mL pear shaped round bottom flask and dissolved in 25 mL deionized water with stirring. The flask was fitted with a pressure equalizing dropping funnel loaded with five equivalents of the counter-ion exchange salt (lithium bis(trifluoromethanesulfonimide) or ammonium hexafluorophosphate) dissolved in 25 mL of deionized water. The solution was added dropwise to the functionalized bipyridinium solution. During this addition, an off-white precipitate or oil began to form. After complete addition of the counterion solution, the reaction mixture was heated to 60° C. and stirred overnight. The mixture was cooled in an ice bath, then the solid was isolated by vacuum filtration, and washed 3×25 mL volumes of deionized water.

Figure 24:
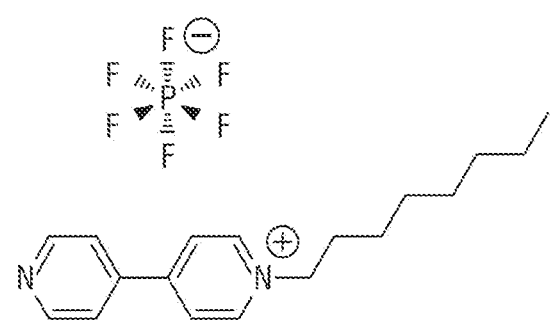
FIG. 24 is a diagram of a twenty-third chemical structural formula showing a bipyridinium form with a suitable anion that may perform as a liquid electrolyte for a redox flow battery in accordance with the present invention.

A second general method for preparation of mono-substituted bipyridine salts such as shown in FIGS. 24: A solution of 4,4'-bipyridine (2.00 g, 12.8 mmol) and n-iodooctane (1.18 g, 6.40 mmol) were combined with 25 mL of toluene in a 100-mL round bottom flask and a stir bar. The mixture was heated to 85° C. and stirred overnight. Upon cooling, the orange solid was collected by vacuum filtration and washed with 25 mL toluene and 3×50 mL of diethyl ether. The desired mono-substituted product was purified by column chromatography using silica gel and 10:1 dichloromethane in methanol (volumetric ratio). The resulting yellow/orange solid was transferred to a 100-mL pear shaped round bottom flask and dissolved in 25 mL deionized water with stirring. The flask was fitted with a pressure equalizing dropping funnel loaded with five equivalents of ammonium hexafluorophosphate dissolved in 25 mL of deionized water. The solution was added dropwise to the functionalized bipyridinium solution. During this addition, an off-white precipitate began to form. After complete addition of the counterion solution, the reaction mixture was heated to 60° C. and stirred overnight. The mixture was cooled in an ice bath, the solid was isolated by vacuum filtration, and washed 3×25 mL of deionized water.

For the materials, the general cyclic voltammetry procedure is accomplished with all cyclic voltammograms being acquired using a glassy carbon working electrode (3.0 mm), a platinum counter electrode (coil), and a $Ag/Ag^+$ reference electrode (reference solution: silver wire in 0.1 M tetrabutylammonium hexafluorophosphate (TBA-PF6) and 0.01 M silver nitrate in acetonitrile). A baseline solution consisting of 0.1 M TBA-PF6 in acetonitrile was scanned at least twice across the full window, from −2.5 V to 1.6 V. This measurement was performed prior to the evaluation of each new material to ensure the system was free of impurities. A solution of 0.1 M TBA-PF6 and 0.01 M of the desired electroactive material was prepared in 10 mL of acetonitrile. The solution was purged with nitrogen gas for two minutes, then nitrogen was maintained in the headspace while collecting scans. The cyclic voltammograms (CVs) were collected over the following windows: −2.5 V to 1.6 V; −1.0 V to 0.0 V; and 0.0 V to 1.6 V. Finally, an internal standard of 0.01 M ferrocene was added to the solution and a cyclic voltammogram was collected of the full window of −2.5 V to 1.6 V. This overall procedure was repeated for each of the electroactive materials. Scan rate studies were performed on select electroactive materials. In this instance, the voltage range was adjusted to isolate the desired redox event and the voltage scan rate was swept at 10, 20, 50, 100, or 200 mV/s.

The measurements of the melting points were accomplished using Differential Scanning calorimetry (DSC) using 40 µL aluminum crucibles that were hermetically sealed with a pinhole. The system is purged with a nitrogen gas flow which is maintained for the duration of the experiment. The samples were subjected to two heating and cooling cycles. The temperature was ramped at 10° C./min from as low as −20° C. up to 300° C. (dictated by sample thermal stability). The heat absorbed or released by the sample was used to identify phase transitions such as melting and crystallization.

The symmetrical viologen derivatives shown in FIGS. 2-7 and 9-12 were prepared by refluxing 4,4'-bipyridine in acetonitrile with the appropriate alkyl halide as explained above followed by counter-anion exchange with either ammonium hexafluorophosphate or lithium bis(trifluoromethylsulfonyl)imide to yield the desired products. The pyridinium protons are found as two doublets between 8 to 10 ppm. In addition, these two doublets of pyridinium protons share the same scalar coupling (or called through-bond coupling) values, which confirm the symmetrical structure property of these viologen derivatives. The alkyl group attached to pyridinium appear between 0.8 to 5.2 ppm while the polyether group linked to pyridinium are observed between 3.0 to 5.0 ppm.

While none of the materials shown in FIGS. 2-12 are room temperature ionic liquids, there are several notable trends in the data that provide insight for viologen core materials as undissolved liquid electrolytes in redox flow batteries.

For consistent cation core structures, the melting point is typically higher when the hexafluorophosphate ($PF_6$) anion is used in place of the triflimide ($NTf_2$) anion. The choice of nitrogen functionality also plays a role in determining the melting point of the materials. Broadly, branched substrates shown in FIGS. 6-10 show higher melting points than their linear counterparts shown in FIGS. 3-5, 11, and 12. For example, the material shown in FIG. 4 which contains a $PF_6$ anion and linear n-octyl nitrogen functionality shows a single melting event at 67° C. while material shown in FIG. 9, which contains the same anion, but which includes a branched 2-ethylhexyl nitrogen chain (same total carbon number) does not melt within the differential scanning calorimetry (DSC) experimental range of 250° C.

Figure 11:
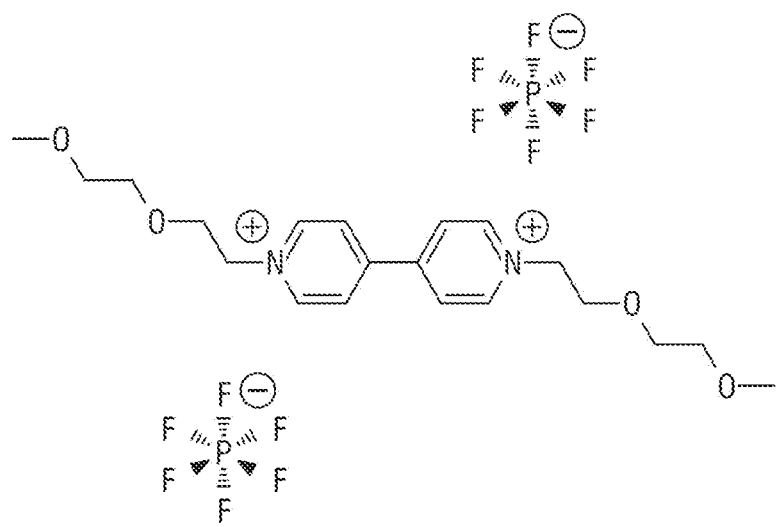
FIG. 11 is a diagram of a tenth chemical structural formula showing a bipyridinium form with a suitable anion that may perform as a liquid electrolyte for a redox flow battery in accordance with the present invention.
Figure 12:
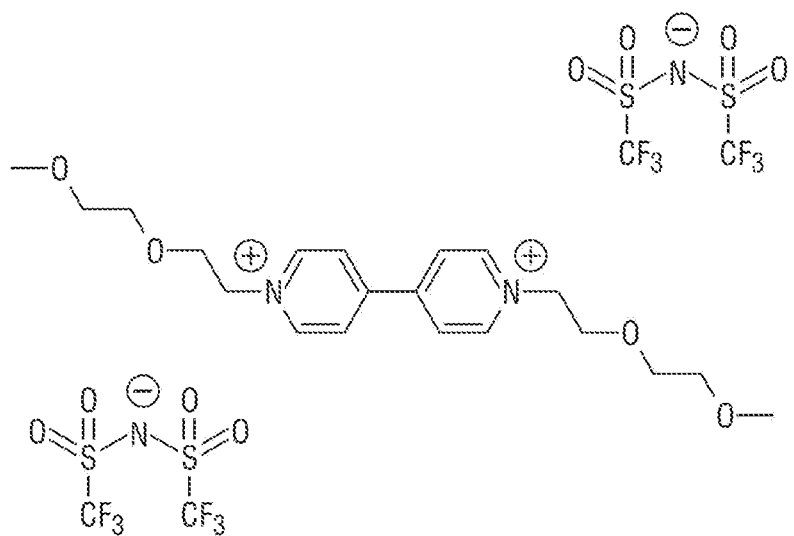
FIG. 12 is a diagram of an eleventh chemical structural formula showing a bipyridinium form with a suitable anion that may perform as a liquid electrolyte for a redox flow battery in accordance with the present invention.
Figure 13:
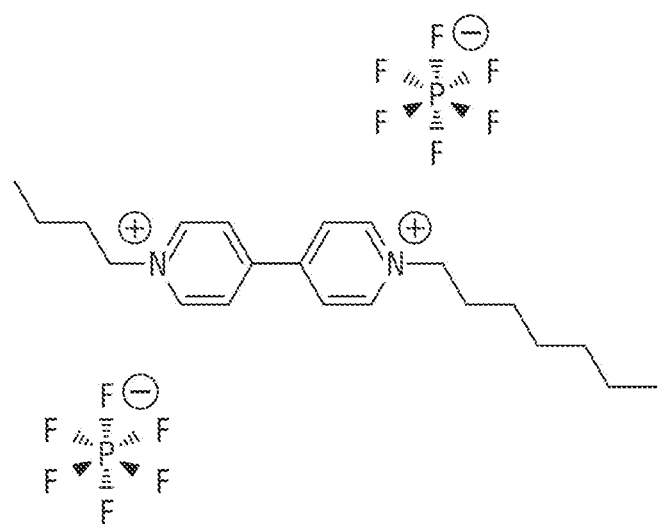
FIG. 13 is a diagram of a twelfth chemical structural formula showing a bipyridinium form with a suitable anion that may perform as a liquid electrolyte for a redox flow battery in accordance with the present invention.
Figure 14:
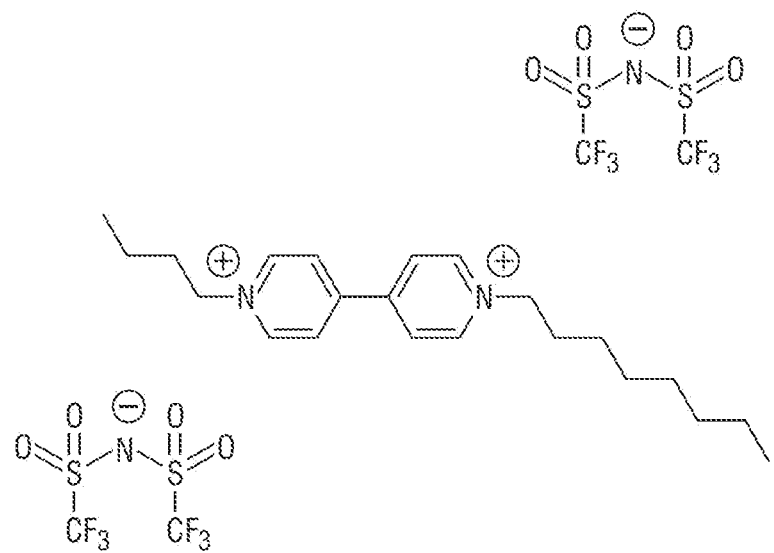
FIG. 14 is a diagram of a thirteenth chemical structural formula showing a bipyridinium form with a suitable anion that may perform as a liquid electrolyte for a redox flow battery in accordance with the present invention.
Figure 15:
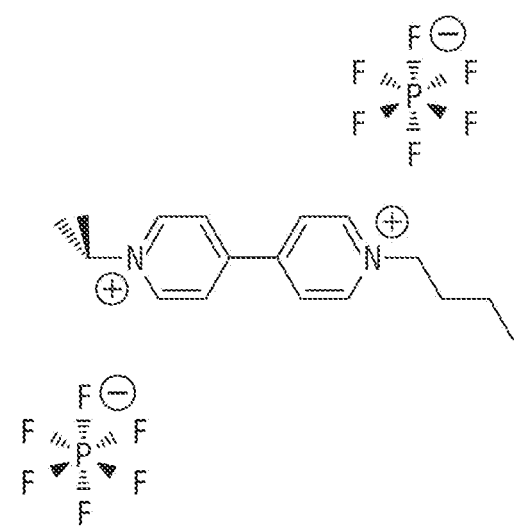
FIG. 15 is a diagram of a fourteenth chemical structural formula showing a bipyridinium form with a suitable anion that may perform as a liquid electrolyte for a redox flow battery in accordance with the present invention.
Figure 16:
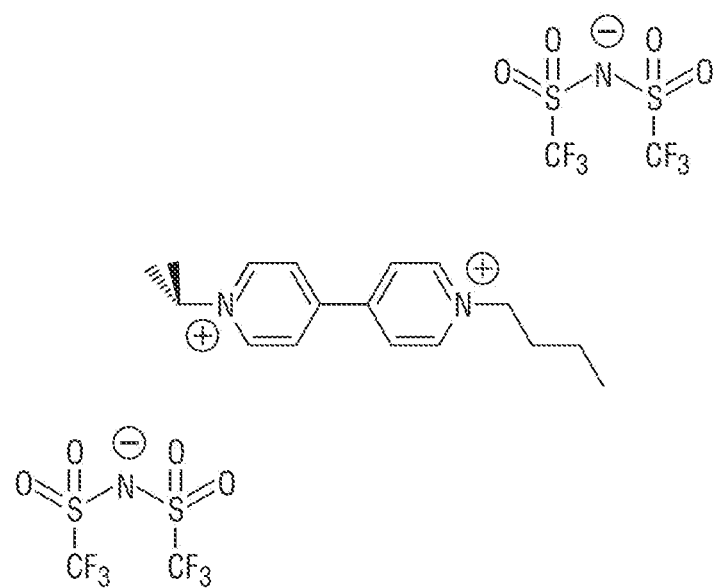
FIG. 16 is a diagram of a fifteenth chemical structural formula showing a bipyridinium form with a suitable anion that may perform as a liquid electrolyte for a redox flow battery in accordance with the present invention.
Figure 17:
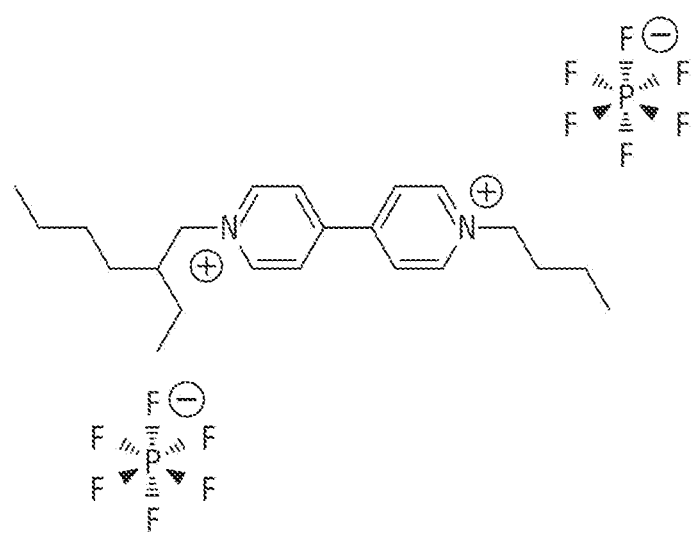
FIG. 17 is a diagram of a sixteenth chemical structural formula showing a bipyridinium form with a suitable anion that may perform as a liquid electrolyte for a redox flow battery in accordance with the present invention.
Figure 18:
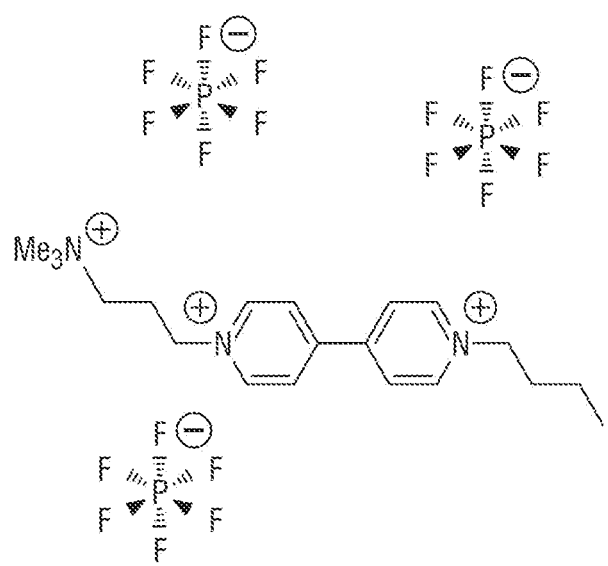
FIG. 18 is a diagram of a seventeenth chemical structural formula showing a bipyridinium form with a suitable anion that may perform as a liquid electrolyte for a redox flow battery in accordance with the present invention.
Figure 19:
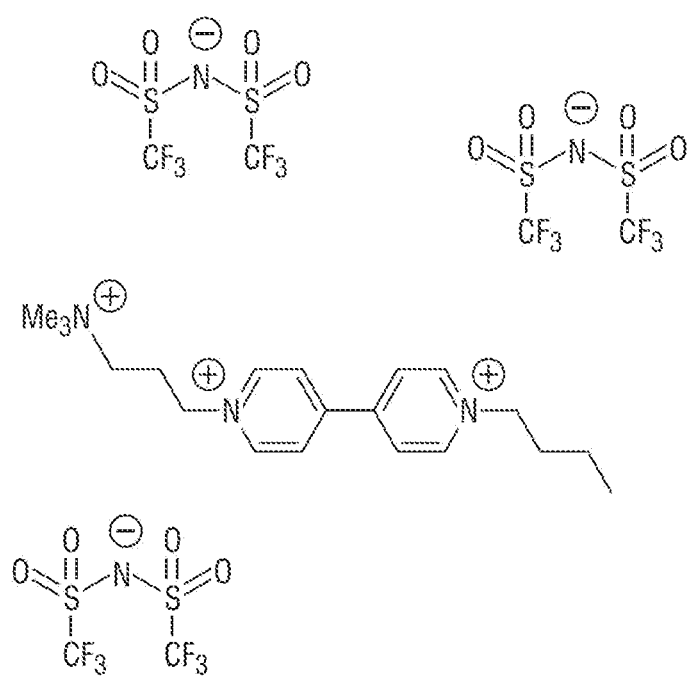
FIG. 19 is a diagram of an eighteenth chemical structural formula showing a bipyridinium form with a suitable anion that may perform as a liquid electrolyte for a redox flow battery in accordance with the present invention.
Figure 20:
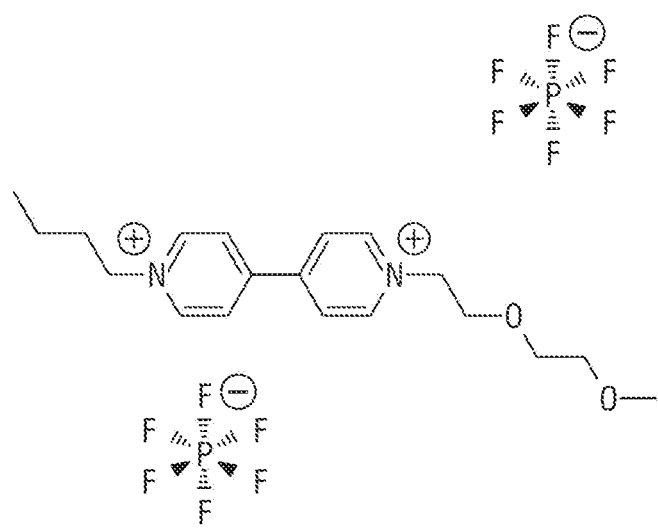
FIG. 20 is a diagram of a nineteenth chemical structural formula showing a bipyridinium form with a suitable anion that may perform as a liquid electrolyte for a redox flow battery in accordance with the present invention.

The materials shown in FIGS. 11 and 12 were prepared in an effort to generate a room temperature ionic liquid (RTIL). Surprisingly, these materials recorded melting points of 117° C. and 99° C. with $PF_6$ and $NTf_2$ anions, respectively. Contrary to expectations, these melting points are higher than the alkyl analogues shown in FIGS. 4 and 5. Based on the melting points of this set of target molecules, it appears that symmetrically functionalized bipyridiniums are less desirable candidates for generating RTILs. Ultimately, while these insights are helpful, melting points for materials that are closer to ambient temperatures are believed to be necessary for practical application as a non-solvated redox active flow battery electrolyte. However, it is envisioned that systems to heat electrolytes could be envisioned to enable use of marginal melt temperature, high-performance electrolytes.

The electrochemical properties of the materials were assessed in acetonitrile by Cyclic Voltammetry as described above with 0.1 M TBA-$PF_6$ supporting electrolyte and ferrocene internal standard. Electrochemical data are reported for the practical embodiments of the present in Table 4 above.

Materials shown in FIGS. 13 through 21 were prepared by a stepwise synthetic procedure where 4,4'-bipyridine was first reacted with excess n-iodobutane in toluene to give exclusively 1-(n-butyl)-4,4'-bipyridinium iodide in high purity and yield. The intermediate is then reacted with excess of the second alkyl halide, in acetonitrile, followed by anion exchange with the desired counter-anion.

As with previous samples, the melting points of the materials shown in FIGS. 13-21 were assessed by Differential Scanning calorimetry as described above. Consistent with previous findings, the melting points of $NTf_2$ salts were almost always lower than their corresponding $PF_6$ counterparts. By incorporating asymmetry into the molecules, several materials were generated with a melting point below 50° C. as embodied by materials shown in FIGS. 13, 14, 16, and 21 and set forth in Table 1 above. It is still more preferable to have a melting temperature be lower such as below about 45° C. and more preferably below 35° C. The 50° C. melt temperature is a significant improvement over the symmetrical analogues 2-12 but there is no apparent structural feature that can be attributed to the lower melting point and used for the rational design of future molecules for redox flow batteries. In the case of the material shown in FIG. 21, substitution of the bipyridine with n-butyl and poly-ether functional groups coupled with the $NTf_2$ anion yielded a viscous, room temperature ionic liquid.

Figure 25:
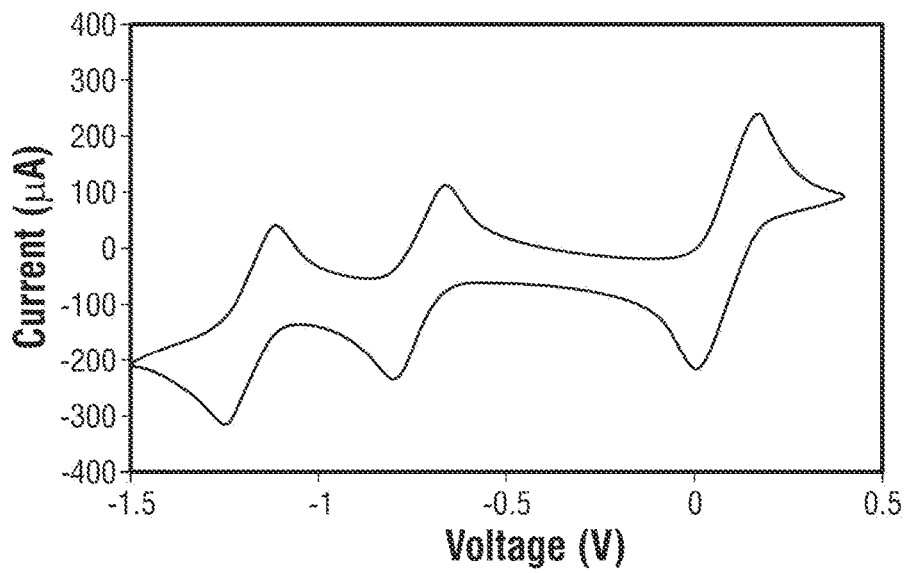
FIG. 25 is a cyclic voltammogram diagram of the twentieth bipyridinium electrolyte shown in FIG. 21 assessed with a ferrocene internal standard at 0.17V.
Figure 26:
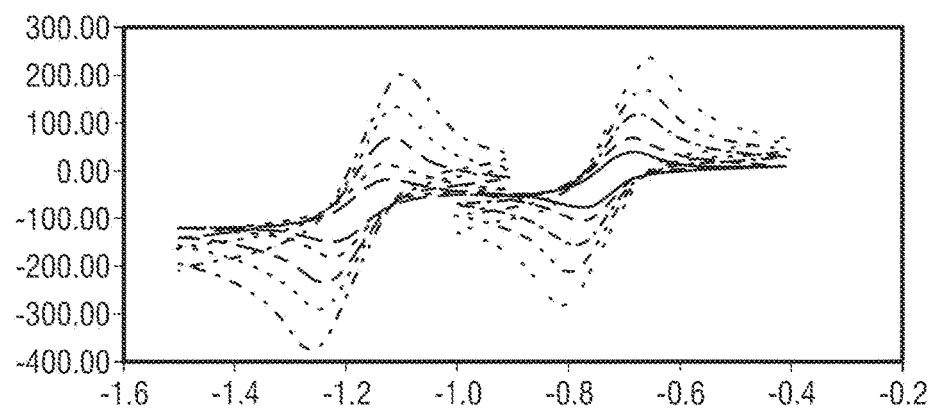
FIG. 26 is a diagram of a scan rate study of the twentieth bipyridinium electrolyte shown in FIG. 21.

The electrochemical properties of materials 13 through 21 were assessed in acetonitrile by cyclic voltammetry with 0.1 M TBA-$PF_6$ supporting electrolyte and ferrocene internal standard. Electrochemical data are reported in Table 5 and a representative cyclic voltammetry and scan rate study of the material shown in FIG. 21 are shown in FIGS. 25 and 26. Similar to the symmetrically substituted materials, electrochemical analysis of these molecules yielded two quasi-reversible redox events in the ranges of −0.79 V to −0.83 V and −1.22 V to −1.28 V with peak current ratios close to parity. Again, this result indicates a high degree of electrochemical stability and demonstrates that the electrochemistry is independent of the choice of counter-anion and nitrogen functional group.

Given that material shown in FIG. 21 has reversible electrochemistry on the cyclic voltammetry timescale and is liquid at room temperature, it is an attractive electrolyte for a redox flow battery without solvent or with some minimal concentration of solvent such as 5 mM of acetonitrile or less.

In assessing monosubstituted 1-alkyl-4,4'-bipyridinium salts, mono-n-butyl substituted materials shown in FIGS. 22 and 23 were prepared by reacting 4,4'-bipyridine with excess n-iodobutane in toluene to give exclusively 1-(n-butyl)-4, 4'-bipyridinium iodide in high purity and yield. This material was then subjected to anion exchange to give the $PF_6$ and $NTf_2$ salts.

An isolated room temperature ionic liquid consisting of 1-(n-butyl)-4,4'-bipyridinium triflimide shown in FIG. 23 while a $PF_6$ derivative was isolated as a solid with a melting point of ~129° C. as shown in Table 1. Conversely, the reaction of n-iodooctane with 4,4'-bipyridine afforded a mixture of the mono- and di-alkylated products which could be further purified via column chromatography. Anion exchange of the mono-alkylated material with ammonium hexafluorophosphate yielded the material shown in FIG. 24 where the melting point analysis showed a melting event at ~80° C. While a $NTf_2$ salt was not evaluated, it is believed that it too would be an interesting material for consideration as an electrolyte in a redox flow battery.

Figure 27:
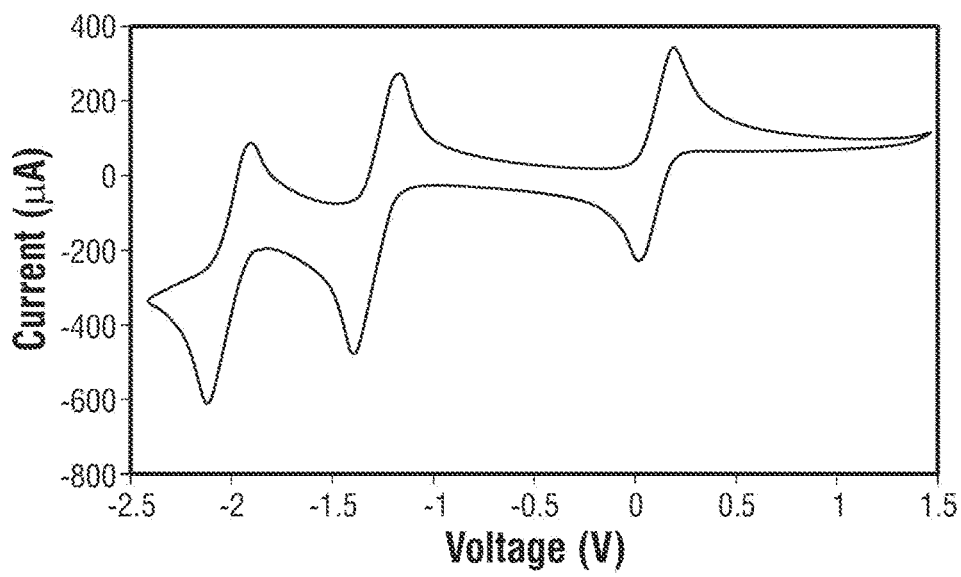
FIG. 27 is a cyclic voltammogram diagram of the twenty-second bipyridinium electrolyte shown in FIG. 23 assessed with a ferrocene internal standard at 0.17V.
Figure 28:
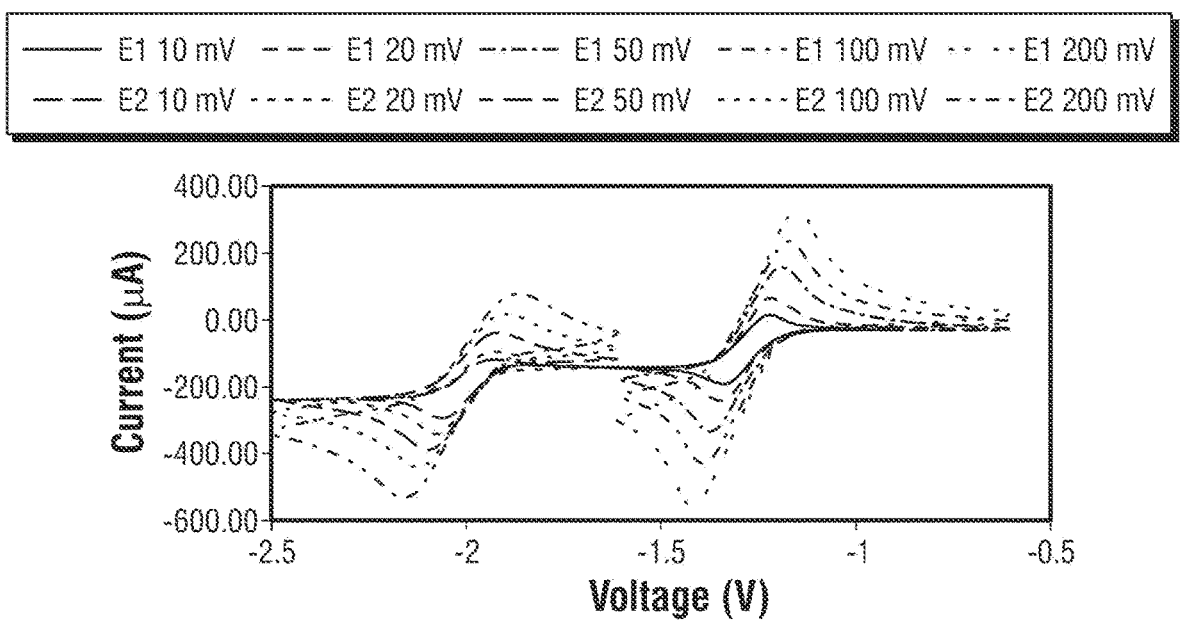
FIG. 28 is a diagram of a scan rate study of the twenty-second bipyridinium electrolyte shown in FIG. 23.

The electrochemical properties of materials shown in FIGS. 22, 23, and 24 were assessed in acetonitrile by Cyclic Voltammetry with 0.1 M TBA-$PF_6$ supporting electrolyte and ferrocene internal standard. Electrochemical data are reported in Table 5 and a representative CV and scan rate study of the material shown in FIG. 23 are shown in FIGS. 27 and 28. Consistent with the di-substituted viologen analogues, these materials display two redox events in the ranges of −1.36 V to −1.43 V and −2.10 V to −2.16 V, respectively.

Essentially solvent free means that the redox active bipyridinium may include an insignificant volume of solvent. Less than 1% by weight solvent added to the electrolyte would certainly be insignificant. Higher than 15% would begin to be significant. Solvent content of 5% or more would not be preferred but would not be significant either. Less than 3% would be more preferred and further reduction of solvent would provide diminishing benefits as the concentration of the electrolyte and energy density would not increase by much. Basically, it is recognized that one could add solvent while essentially practicing the invention and taking advantage of the high energy concentration of the these RTILs.

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A process for making a redox flow battery comprising the steps of:
    converting a bipyridinium solid to a bipyridinium containing ionic material that is liquid at a temperature below 70° C. by appending at least one substituent group to the bipyridinium where the at least one added substituent group lowers the melting temperature of the resulting bipyridinium ionic material;
    providing an anolyte and a catholyte where one of the anolyte and catholyte comprises the bipyridinium ionic material from the previous step; and
    providing a catholyte storage tank for storing the catholyte, an anolyte storage tank for storing the anolyte, a power cell arranged for catholyte and anolyte to coexist and be physically separated while also in ion communication with one another, a catholyte pump to circulate the catholyte from the catholyte storage tank to the power cell and back to the catholyte storage tank; and an anolyte pump to circulate anolyte from the anolyte storage tank to the power cell and back to the anolyte storage tank.

2. The process for making a redox flow battery according to claim 1 wherein the step of appending a substituent group to the bipyridinium ionic material comprises appending an n-butyl substituent group to the bipyridinium ionic material.

3. The process for making a redox flow battery according to claim 1 wherein the step of appending a substituent group to the bipyridinium ionic material comprises appending a poly ether substituent group to the bipyridinium ionic material.

4. The process for making a redox flow battery according to claim 1 wherein the step of appending a function group to the bipyridinium ionic material comprises appending a substituent group to the nitrogen constituent of a 4,4'-bipyridinium ionic material.

5. The process for making a redox flow battery according to claim 1 wherein the step of converting a bipyridinium containing ionic material further comprises adding a triflimide anion liquid.

6. The process for making a redox flow battery according to claim 1 wherein the anolyte or catholyte containing the bipyridinium ionic material comprises at least 80% active bipyridinium ionic liquid and no more than 20% by weight of diluent or solvent.

7. The process for making a redox flow battery according to claim 1 wherein the anolyte or catholyte containing the bipyridinium viologen comprises at least 90% active viologen based ionic liquid and no more than 10% diluent or solvent.

8. The process for making a redox flow battery according to claim 1 wherein the anolyte or catholyte containing the bipyridinium comprises more than 95% active viologen based ionic liquid and no more than 5% of any other chemical.

9. The process for making a redox flow battery according to claim 1 where the step of appending the substituent group more particularly reduces the melting point of the ionic liquid to a temperature of 50° C. or less.

10. The process for making a redox flow battery according to claim 1 where the step of appending the substituent group more particularly reduces the melting point of the ionic liquid to a temperature below 45° C.

11. The process for making a redox flow battery according to claim 1 where the step of appending the substituent group more particularly reduces the melting point of the ionic liquid to a temperature below 35° C.

12. The process for making a redox flow battery according to claim 1 where the step of appending the substituent group to the bipyridinium more particularly comprises appending the substituent group to the nitrogen constituent of a 4,4'-bipyridinium and wherein the substituent group is an alkyl substituent group.

13. The process for making a redox flow battery according to claim 12 where the step of appending the substituent group to the bipyridinium more particularly comprises appending two substituent groups, one at either end of the 4,4'-bipyridinium wherein both substituent groups are alkyl function groups.

14. The process for making a redox flow battery according to claim 13 where the step of appending the two substituent groups to the 4,4'-bipyridinium molecular core appends different substituent groups at each end of the molecule.

15. The process for making a redox flow battery according to claim 12 where the step of appending the substituent group to the 4,4'-bipyridinium more particularly comprises appending an n-butyl substituent group to one end of the bipyridinium.

16. The process for making a redox flow battery according to claim 12 where the step of appending the substituent group to the 4,4'-bipyridinium more particularly includes appending an n-octyl substituent group.

17. The process for making a redox flow battery according to claim 1 wherein the where the step of appending the substituent group to the bipyridinium more particularly comprises appending a substituent group to each of the nitrogen constituents of a 4,4'-bipyridinium and more particularly comprises appending different substituent groups to each end of the 4,4'-bipyridinium.

18. The process for making a redox flow battery according to claim 1 where the step of appending the substituent group to the bipyridinium more particularly comprises appending the substituent group to the nitrogen constituent of a 4,4'-bipyridinium and wherein the substituent group is a polyether substituent group.

* * * * *